(12) United States Patent
Jamiolkowski et al.

(10) Patent No.: US 6,981,944 B2
(45) Date of Patent: Jan. 3, 2006

(54) IMPLANTABLE SURGICAL MESH HAVING A LUBRICIOUS COATING

(75) Inventors: Dennis D. Jamiolkowski, Long Valley, NJ (US); Andrea Slater-Tomko, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/878,159

(22) Filed: Jun. 28, 2004

(65) Prior Publication Data

US 2005/0010078 A1   Jan. 13, 2005

Related U.S. Application Data

(60) Provisional application No. 60/485,271, filed on Jul. 7, 2003.

(51) Int. Cl.
*A61F 2/02* (2006.01)
*A61B 19/00* (2006.01)

(52) U.S. Cl. .......................... 600/30; 128/898

(58) Field of Classification Search .............. 600/29, 600/30, 37, 135; 602/4; 606/144, 145; 442/327, 442/118, 164, 170, 171; 607/105; 604/113; 128/898

See application file for complete search history.

(56) References Cited

U.S. PATENT DOCUMENTS

| | | | | |
|---|---|---|---|---|
| 5,150,706 A | * | 9/1992 | Cox et al. | 607/105 |
| 5,899,909 A | | 5/1999 | Claren et al. | |
| 5,976,995 A | * | 11/1999 | Palmer, Jr. | 442/118 |
| 6,306,079 B1 | * | 10/2001 | Trabucco | 600/30 |
| 6,475,139 B1 | * | 11/2002 | Miller | 600/135 |
| 6,491,703 B1 | | 12/2002 | Ulmsten | |
| 6,596,001 B2 | * | 7/2003 | Stormby et al. | 606/144 |
| 6,652,450 B2 | * | 11/2003 | Neisz et al. | 600/30 |
| 2001/0049467 A1 | * | 12/2001 | Lehe et al. | 600/30 |
| 2002/0072694 A1 | * | 6/2002 | Snitkin et al. | 602/4 |
| 2003/0149440 A1 | | 8/2003 | Kammerer et al. | |
| 2003/0220039 A1 | * | 11/2003 | Chen et al. | 442/327 |
| 2005/0027220 A1 | | 2/2005 | Wagner et al. | |

* cited by examiner

*Primary Examiner*—Samuel G. Gilbert

(57) ABSTRACT

Implantable surgical meshes are disclosed. The mesh is attached to a needle and is coated with a lubricious material in such a manner that the coating reduces friction and trauma as the mesh is implanted, and subsequently is substantially eliminated once the mesh is implanted to enable better tissue ingrowth into the mesh. Methods of placing such a mesh are also disclosed.

12 Claims, 2 Drawing Sheets

IMPLANTABLE SURGICAL MESH HAVING A LUBRICIOUS COATING

CROSS REFERENCE TOP RELATED APPLICATION

The present application claims the benefit of U.S. Provisional Patent Application No. 60/485,271, which was filed Jul. 7, 2003.

BACKGROUND OF THE INVENTION

1. Field of the Invention

The present invention relates generally to implantable surgical meshes, and more particularly, to implantable surgical meshes that are coated with a lubricious material in such a manner that the coating reduces friction and trauma as the mesh is implanted, and subsequently is substantially eliminated once the mesh is implanted to enable better tissue ingrowth into the mesh.

2. Background Discussion

Implantable surgical meshes have been widely used for a variety of different surgical procedures such as hernia repair, pelvic floor repair, urethral slings for treating incontinence, and many others. In some applications, such as urethral slings, implantation is accomplished without an open surgery, but rather by passing a relatively thin piece of mesh into the body following the path of a needle. One such method for placing a urethral sling is described in detail in U.S. Pat. No. 5,899,909, which is incorporated herein by reference in its entirety. U.S. Pat. No. 5,899,909 discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra.

When passing the mesh through the body in such a manner, an unprotected mesh, due to its rough abrasive surface will often irritate the surrounding tissue it is being passed through. However, once the mesh is properly placed, it is important to have an exposed mesh structure to promote sufficient tissue ingrowth to thereby secure the mesh in place against future movement. Thus, there are competing interests: on the one hand a desire to reduce as much as possible irritation of surrounding tissue as the mesh is passed into the body, and on the other hand, the desire to have an open mesh structure once properly placed to promote the maximum amount of tissue ingrowth possible.

As described in U.S. Pat. No. 6,491,703 one way in which both objectives have been achieved is by providing a sheath that substantially surrounds the mesh as it is implanted, but then is subsequently removed after the tape is positioned to allow for the proper tissue ingrowth. As described, the sheath must be removed from the respective ends of the tape, and thus there is some degree of tension or movement of the tape following placement, and any such movement is undesirable.

Accordingly, it would be desirable to provide a mesh for implantation into the body, that reduces tissue trauma while inserted, yet provides an open mesh structure following implantation to ensure proper tissue ingrowth.

SUMMARY OF THE INVENTION

The invention overcomes the deficiencies of the prior art and provides for an implantable surgical mesh that is coated with a lubricious material in such a manner that the coating reduces friction and trauma as the mesh is implanted and adjusted, and subsequently is substantially eliminated once the mesh is implanted to enable better tissue ingrowth into the mesh. It comprises a mesh and a curved needle having a proximal end, with the proximal end being releasably attached to the mesh, and wherein the mesh has an effective amount of a lubricious coating. The coating can be either dispersed over the outer surface of the mesh so as to form a smooth outer surface around the mesh, or it can be dispersed on the individual fibers of the mesh before the mesh is woven or knitted. The mesh can be either non-absorbable or bio-absorbable, or a combination of absorbable and non-absorbable fibers.

Methods for placement of the mesh are also described. In one embodiment, the method comprises the following steps: a) providing a mesh having a needle attached to the mesh and a bio-absorbable lubricious coating on the surface of the mesh or on the individual fibers of the mesh before the mesh is woven or knitted into its final configuration; b) implanting the mesh in a patient; and c) leaving the mesh implanted within the patient at least until the lubricious coating is bio-absorbed. In an alternate embodiment, the method comprises the following steps: a) providing a mesh having a needle attached to the mesh and a bio-absorbable lubricious coating on the surface of the mesh or on the individual fibers of the mesh before the mesh is woven into its final configuration; b) implanting the mesh in a patient; and c) irrigating the mesh implanted within the patient until the lubricious coating is removed.

An advantage of the invention is that it is useful across different medical specialties depending on preferred surgical approaches. In particular, the implantable surgical device of this invention is particularly well suited for the treatment of female incontinence.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description.

The invention as illustrated may be implemented or incorporated in other embodiments, variations and modifications, and may be practiced or carried out in various ways.

The coated mesh of this invention is especially adapted for implantation into the body for treating incontinence. A coated mesh or tape is passed through pelvic tissue and positioned between the urethra and vaginal wall, creating a supportive sling. Once properly placed, the coating is dissolved or absorbed as a result of contact with the tissue, or otherwise removed, allowing the mesh to provide the structural support for tissue ingrowth and enhanced support for the urethra. When pressure is exerted upon the lower abdomen, such as during a cough or sneeze, the mesh provides support to the urethra, allowing it to keep its seal and prevent the unwanted discharge of urine.

Figure 1:
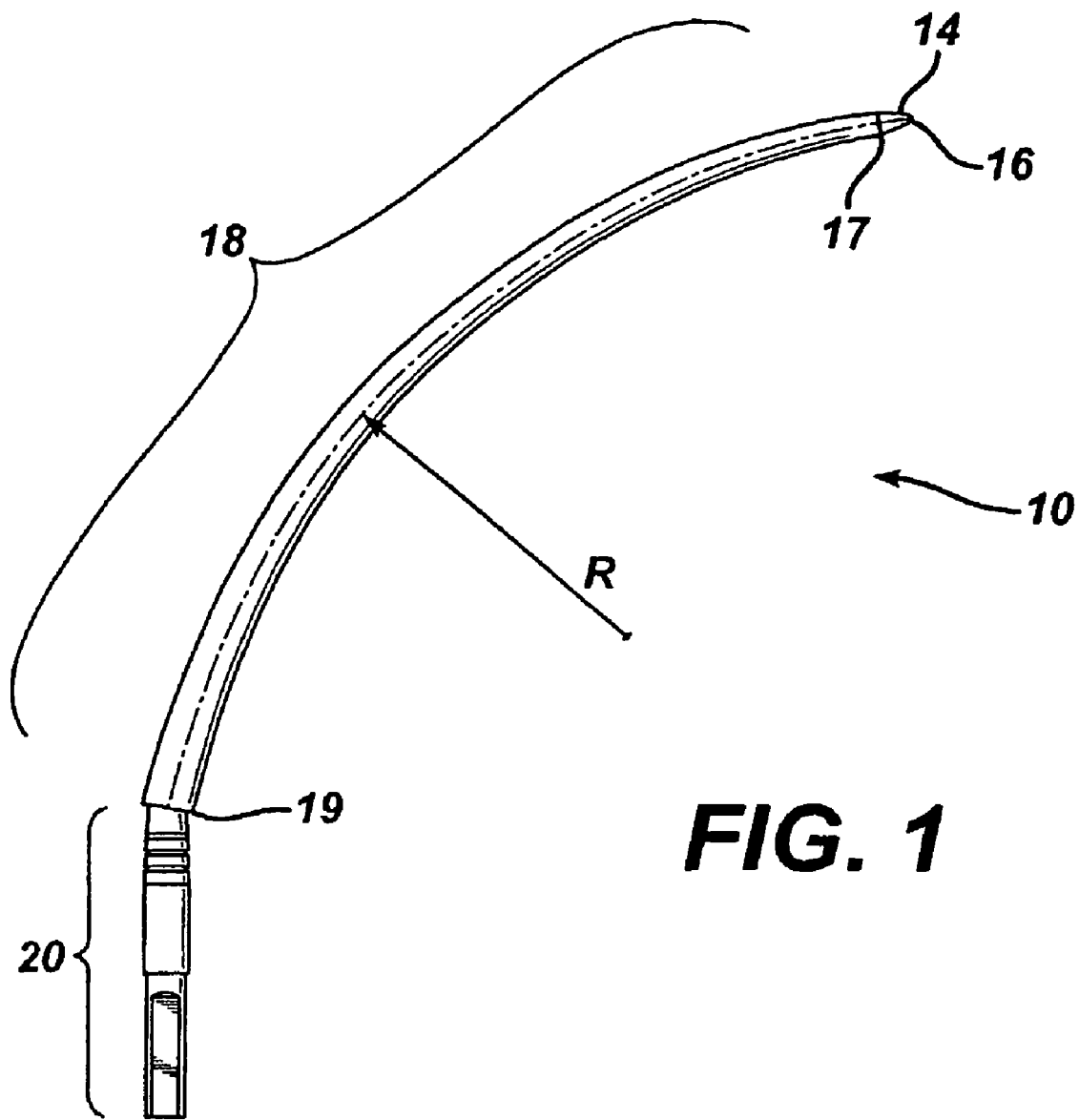
FIG. 1 is a side view of the needle portion of the current invention.
Figure 2:
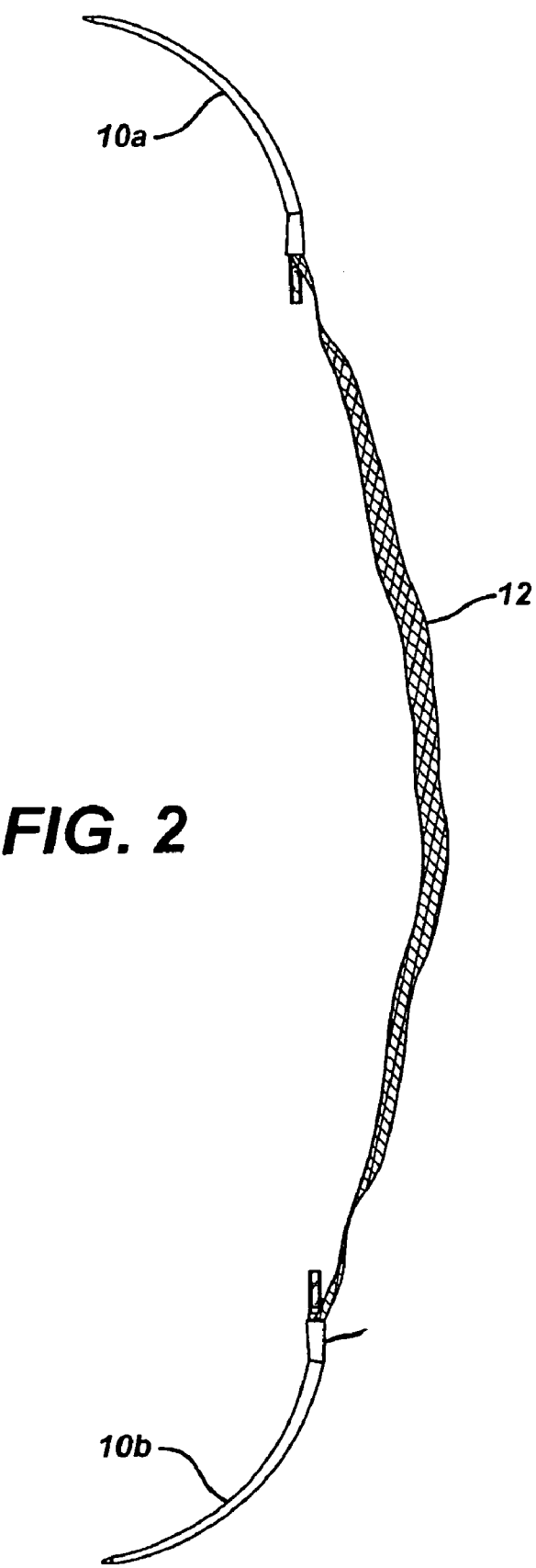
FIG. 2 is side view of two needles and a tape, or mesh, interconnecting the needles.

Referring to FIGS. 1 and 2, there is shown the preferred surgical device of the invention. The surgical device has a needle 10 that is attached at its proximal end to a mesh 12 at either end of the mesh. The distal end of needle 10 terminates at a conical section 14 having a tip 16. Alternate configurations, such as a blade-like, arrow or burr tips are also possible. A blunt tip is preferred since it is less likely to stick in bone or penetrate bladder wall tissue or blood vessel wall tissue as will be appreciated from the method of implanting the mesh as described below. When the method according to the invention is practiced, two needles 10A and 10B of the embodiment described shall be connected one at each end of the mesh 12, as shown in FIG. 2.

The proximal end of needle 10 terminates in an attachment segment 20 that is adapted to mate and lock into a handle as disclosed in U.S. Pat. No. 5,899,909. The preferred curvature of the needle and its diameter in order to follow substantially the profile of the pubis between the vagina and the abdominal wall for treating female incontinence is also disclosed in U.S. Pat. No. 5,899,909.

Needle 10 is preferably tubular with a circular cross section and is made from a material that is compatible with the human body. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the mesh 12. The surface of needle 10 may also be darkened in shade or color to provide higher visibility while in place in the body during a cystoscopy.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Mesh 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the mesh 12 is a combination of a synthetic material and a natural material centered between the synthetic material. A still further embodiment of the mesh 12 includes a combination of synthetic material and natural material, where the natural material is placed over or incorporated within a generally central portion of the synthetic material.

One advantage of the mesh configurations is that natural material is along the center region of mesh 12 so that after installation of mesh 12, natural material is positioned below the urethra and eliminates possible erosion issues at the interface of the urethra and mesh. Natural material may be connected to the synthetic material by means of sewing, gluing with biocompatible glue, cell culturing or other known means.

Mesh 12 may be of any convenient shape that suits the intended purpose of the invention. An exemplary width is about 1 cm and the length would be dependent upon the size of the female undergoing the procedure. Mesh 12 may be single or double ply, generally planar in structure, or tubular to provide additional supporting strength and more surface area on which tissue fibers may attach. Moreover, mesh 12 may consist of different types of material, such as a bioabsorbable and non-bioabsorbable material. The mesh may also be made radio-opaque and/or of a contrasting color to the body tissue to allow for future diagnostic visualization. In one embodiment mesh 12 may be attached to needle segment 20 by means of tying, gluing or other suitable attaching means. Preferably, a biocompatible heat shrink tube 36 fixes mesh 12 onto needle portion 20, as shown in FIGS. 1 and 2.

Mesh 12 is coated with a lubricous coating to facilitate the mesh passing through body tissue as will be discussed in more detail below. The coating may be hydrophobic or hydrophilic. Hydrophobic coatings include salts of fatty acids such as calcium stearate. Hydrophilic coatings may be water-soluble or non-water soluble. Additionally, the coating may be synthetic or natural. In a preferred embodiment, the coating is hydrophilic. More specifically, the coating is a water-soluble synthetic polymer. Such water-soluble polymers include polyacrylamides, polyvinyl pyrrolidone (PVP), polyvinyl alcohol, polyvinyl methyl ether, polyethylene oxide, polyethylene glycol, polyacrylic acid and their salts, and various chemical derivatives of cellulose, such as carboxymethylcellulose.

As previously stated, of particular utility are hydrophilic synthetic absorbable polymers that are water-soluble; that is, the polymers migrate from the site by a combination of absorption and water dissolution. Members of the polyoxaester coating family, based on polyglycol diacid (depicted by the chemical formula below), and polyethylene glycol diols, provide such features.

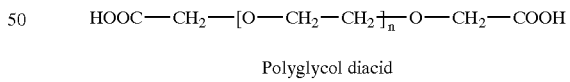

Polyglycol diacid

Thus a water soluble polyoxaester can be prepared by polycondensation using polyethylene glycol diol with a molecular weight of 200 Daltons, and a small amount of ethylene glycol and polyglycol diacid having a molecular weight of about 600 Daltons. The resulting polyester is both absorbable and water-soluble. The molecular weight of the polyester can be controlled by conventional means. Higher molecular weight resin will remain for a longer period of time on the mesh. Alternately, the polyoxaester can be further modified by polymerization with lactone monomers using ring-opening techniques. Useful lactone monomers include glycolide, lactide, p-dioxanone, trimethylene carbonate and ε-caprolactone. Of particular utility is copolymerization with glycolide. Copolymerizing with lactone will alter water solubility and dissolution rates, as well as absorption rates.

Methods for coating the mesh and its fibers will now be described. In one embodiment, the coating would be applied to the individual fibers of the mesh before the mesh is knitted or woven into its final configuration. The fibers could be coated by conventional means including dip coating and melt coating, or any other method known to those skilled in the art. In the case of dip coating, the individual fibers are dipped into a solution of the coating resin dissolved in an appropriate solvent. The fibers are then typically subjected to drying means to remove the solvent. In the case of melt coating, it is typical for the coating to be applied to the fibers in a heated state and the resulting coated fibers allowed to cool. Once the fibers are coated, the mesh would then be manufactured by knitting or weaving the fibers, or by any other method of manufacture of a mesh known to those skilled in the art. In an alternate embodiment, rather than coating the fibers prior to mesh manufacture, the constructed mesh is coated. For example, the mesh is dip-coated or melt-coated, as opposed to coating the constituent fibers prior to mesh fabrication by knitting or weaving the pre-coated fibers.

When the coating is applied to the constituent mesh fibers prior to mesh fabrication, the amount of the coating applied to the fibers effective to provide a lubricious mesh surface for sliding the mesh through tissue should be between about 0.1 to about 15 weight percent of the mesh. Less than about 0.1 weight percent will likely be ineffective for providing a lubricious surface during placement. More than about 15 weight percent could have an adverse impact on the handling properties of the mesh. The preferred range is between about 1 to about 6 weight percent of the coating on the mesh. For the preferred water-soluble polyoxaester coatings, the most preferred range is between about 2 to about 5 weight percent of the coating on the mesh.

In an alternate embodiment, the coating would be provided to fill in the interstices of the tape to render the tape more film-like. In this embodiment, the mesh would be coated after the mesh fibers have been knitted or woven. The coating could be applied by multiple dip coating, by melt coating or by any other means known to one skilled in the art.

The amount of the coating applied to the mesh effective to provide a film-like lubricious mesh surface for sliding the mesh through tissue should be between about 5 to about 50 weight percent of the mesh. Less than about 5 weight percent will likely be ineffective for providing a film-like lubricious surface. More than about 50 weight percent could have an adverse impact on the handling properties of the mesh. The preferred range is between about 10 to about 30 weight percent of the coating on the mesh. For the preferred water-soluble polyoxaester coatings, the most preferred range is between about 15 to about 25 weight percent of the coating on the mesh. Once coated, the surgical device of the present invention would appear to be a substantially smooth film during insertion but would convert to a mesh-like structure after insertion and upon removal of the coating, as will be described in more detail below. These and various other means of coating the fibers of the mesh will be evident to those skilled in the art.

Additionally, the coating may contain an antimicrobial additive to prevent or minimize infection. One such antimicrobial agent is known as triclosan. Coatings that may be useful include those described in U.S. Pat. No. 6,514,517, which is hereby incorporated by reference in its entirety.

As stated previously, the lubricious coating is useful to facilitate the sliding of the mesh through body tissue. Once the mesh is placed, however, it is important to have an exposed mesh structure to promote sufficient tissue ingrowth to thereby secure the mesh in place against future movement. Thus it is important to remove the coating once placement of the mesh has been accomplished. In one embodiment, this is accomplished by having the coating dissolve in body fluids present in the surgical site after placement of the mesh. In an alternate embodiment, removal of the coating is accomplished by chain cleavage or chemical or enzymatic hydrolysis of the coating, followed by dissolution of the by-products by body fluids. In yet another embodiment, removal of the coating is accomplished by washing the coated mesh or by irrigation of the coated mesh once it has been placed in the desired location in the body. This type of removal of the coating is facilitated by providing an irrigation means in the form of an irrigating catheter positioned substantially along the length of the device, whereby the catheter has a plurality of openings along its length. A saline rinse, or other type of fluid rinse, is introduced into the catheter, and then distributed through the plurality of openings, thereby dissolving and dispersing the soluble coating.

The rate of coating removal, which can affect the lubricity of the coating, is also an important factor when placing and adjusting the position of the mesh. This can be controlled by a number of parameters including the composition of the coating and its molecular weight. For example, a polyethylene glycol of about 400 Daltons molecular weight will provide a slippery surface but may be removed from the site rather readily. Higher molecular weight polyethylene glycol resins, such as 4,000 Daltons, although still lubricious, will dissolve more slowly. Although very high molecular weight polyethylene glycol resins, such as 60,000 Daltons, will take longer to dissolve, they may not be as lubricious as the lower molecular weight analogs. Combinations of different molecular weights could tailor the lubricity and removal rate profiles of the coating from the mesh. For example one might use a polyethylene glycol coating of 80 weight-percent 400 Dalton polyethylene glycol with 20 weight-percent 4,000 Dalton polyethylene glycol.

Preferred synthetic absorbable coatings are made of synthetic absorbable polymers that have a fast absorption time. These preferred synthetic absorbable polymers may be copolymeric in nature. The absorption rate of these synthetic polymers can be controlled in part by the composition of the polymer. Compositions of synthetic absorbable copolymers rich in glycolide absorb at faster rates than do synthetic absorbable copolymers rich in lactide, for example. For a given composition, synthetic absorbable polymeric samples of lower crystallinity level tend to absorb faster than well-annealed, high crystallinity polymeric samples.

Mesh 12 can be implanted by any accepted surgical method of placing meshes in the body, such as described in U.S. Pat. No. 5,899,909 and U.S. patent application Ser. No. 2003/0149440 which are hereby incorporated by reference in their entirety. Once mesh 12 is located at each side of the urethra, it is then correctly positioned and tightened under the urethra to prevent urinary incontinence. The surplus of the tape at the outside of the abdominal wall is cut off. The lubricious coating is then eliminated either by the presence of body fluids, or alternatively may be removed by introducing water or other biocompatible fluids into the site. The rate at which the coating is eliminated is dependent upon the type of lubricious coating used, and the combinations of molecular weights as explained previously. The tape is then left as an implant in the body to form an artificial ligament and provide support for the urethra as required in order to restore urinary continence.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method for implanting a mesh within a patient, the method comprising:
    providing a mesh having a mesh surface and being composed of a plurality of woven or knitted fibers, the mesh having a needle attached thereto and a bioabsorbable lubricious coating on either the surface of the mesh or each of the fibers of the mesh before the mesh is woven or knitted;
    implanting the mesh in the patient; and
    irrigating the mesh implanted within the patient until the lubricious coating is removed.

2. The method according to claim 1, wherein the lubricous coating is hydrophilic.

3. The method according to claim 2, wherein the lubricous coating is selected from the group consisting polyacrylamide, polyvinylpyrrolidone, polyvinyl alcohol, polyvinylmethylether, polyethylene oxide, polyethylene glycol, and a mixture of any of these.

4. The method according to claim 1, wherein the amount of the lubricious coating coated on the mesh surface is between about 10 to about 30 weight percent of the mesh.

5. The method according to claim 1, wherein the mesh is used for treating female urinary stress incontinence.

6. A method for implanting a mesh within a patient, the method comprising:
    providing a mesh having a mesh surface and being composed of a plurality of woven or knitted fibers, the mesh having a bioabsorbable lubricious coating on either the surface of the mesh or each of the fibers of the mesh before the mesh is woven or knitted;
    implanting the mesh in the patient; and
    irrigating the mesh implanted within the patient until the lubricious coating is removed.

7. The method according to claim 6, wherein the lubricous coating is hydrophilic.

8. The method according to claim 7, wherein the lubricous coating is selected from the consisting of polyacrylamide, polyvinylpyrrolidone, polyvinyl alcohol, polyvinylmethylether, polyethylene oxide, polyethylene glycol, and a mixture of any of these.

9. The method according to claim 6, wherein the amount of the lubricious coating coated on the mesh surface is between about 10 to about 30 weight percent of the mesh.

10. The method according to claim 6, wherein the mesh is used for treating female urinary stress incontinence.

11. The method according to claim 6, wherein the irrigating step is performed using a catheter.

12. The method according to claim 6, wherein the lubricious coating is comprised of a polyethylene glycol coating of 80 weight-percent 400 Dalton polyethylene glycol with 20 weight-percent 4,000 Dalton polyethylene glycol.

* * * * *

UNITED STATES PATENT AND TRADEMARK OFFICE
CERTIFICATE OF CORRECTION

PATENT NO. : 6,981,944 B2
DATED : January 3, 2006
INVENTOR(S) : Dennis D. Jamiolkowski and Andrea Slater-Tomko It is certified that error appears in the above-identified patent and that said Letters Patent is hereby corrected as shown below:

Column 8,
Line 16, before "consisting," insert -- group --.

Signed and Sealed this

Eighteenth Day of April, 2006

JON W. DUDAS
*Director of the United States Patent and Trademark Office*